(12) United States Patent
Gellman et al.

(10) Patent No.: US 7,947,073 B2
(45) Date of Patent: *May 24, 2011

(54) RESORPTION-CONTROLLABLE MEDICAL IMPLANTS

(75) Inventors: Barry N. Gellman, North Easton, MA (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/604,972

(22) Filed: Oct. 23, 2009

(65) Prior Publication Data

US 2010/0042207 A1 Feb. 18, 2010

Related U.S. Application Data

(63) Continuation of application No. 11/897,016, filed on Aug. 28, 2007, now Pat. No. 7,608,101, which is a continuation of application No. 10/128,214, filed on Apr. 23, 2002, now Pat. No. 7,261,734.

(51) Int. Cl.
*A61F 2/06* (2006.01)
*A61F 2/02* (2006.01)

(52) U.S. Cl. ............. 623/1.44; 623/1.42; 623/23.75

(58) Field of Classification Search ........... 623/1.13, 623/1.21, 1.38, 1.39, 1.4, 1.44, 1.42, 23.75
See application file for complete search history.

(56) References Cited

U.S. PATENT DOCUMENTS

| 3,710,795 | A | 1/1973 | Higuchi et al. |
|---|---|---|---|
| 4,675,174 | A | 6/1987 | Eckenhoff |
| 4,795,644 | A | 1/1989 | Zentner |
| 4,814,183 | A | 3/1989 | Zentner |
| 4,830,855 | A | 5/1989 | Stewart |
| 4,976,967 | A | 12/1990 | McClelland et al. |
| 5,405,317 | A | 4/1995 | Myers et al. |
| 5,418,222 | A | 5/1995 | Song et al. |
| 5,447,724 | A | 9/1995 | Helmus et al. |
| 5,503,844 | A | 4/1996 | Kwiatek et al. |
| 5,510,077 | A | 4/1996 | Dinh et al. |
| 5,551,954 | A | 9/1996 | Buscemi et al. |
| 5,554,182 | A | 9/1996 | Dinh et al. |
| 5,571,166 | A | 11/1996 | Dinh et al. |
| 5,591,224 | A | 1/1997 | Schwartz et al. |
| 5,591,227 | A | 1/1997 | Dinh et al. |
| 5,599,352 | A | 2/1997 | Dinh et al. |
| 5,605,696 | A | 2/1997 | Eury et al. |
| 5,618,899 | A | 4/1997 | Appelt et al. |
| 5,628,785 | A | 5/1997 | Schwartz et al. |
| 5,629,014 | A | 5/1997 | Kwiatek et al. |
| 5,697,967 | A | 12/1997 | Dinh et al. |
| 5,697,976 | A | 12/1997 | Chesterfield et al. |
| 5,756,145 | A | 5/1998 | Darouiche |
| 5,853,745 | A | 12/1998 | Dariouche |
| 5,916,585 | A | 6/1999 | Cook et al. |
| 6,099,562 | A | 8/2000 | Ding et al. |
| 6,120,536 | A | 9/2000 | Ding et al. |
| 6,299,604 | B1 | 10/2001 | Ragheb et al. |
| 6,663,662 | B2 | 12/2003 | Pacetti et al. |
| 2002/0138154 | A1 | 9/2002 | Li et al. |

*Primary Examiner* — Bruce E Snow
(74) *Attorney, Agent, or Firm* — Mayer & Williams PC; David B. Bonham; Keum J. Park

(57) ABSTRACT

Bioresorbable medical implants are designed to have different resorption rates over time or over the topography of the implants. The resorption of the medical implants are controlled by including layers having differing resorption rates. The layers resorb sequentially over time through sequential exposure to body fluids. A resorption-controllable medical implant includes a series of two or more layers. The first layer includes a first bioresorbable material. The second layer includes a second bioresorbable material and resorbable particles of a first kind dispersed within the second bioresorbable material. Additional layers of bioresorbable material alone or including resorbable particles may be added to slow or speed resorption and achieve desired control over the resorption of the implant. Resorbable particles can be added in differing amounts or kinds in various segments of the implant to provide topographically differing resorption rates.

18 Claims, 7 Drawing Sheets

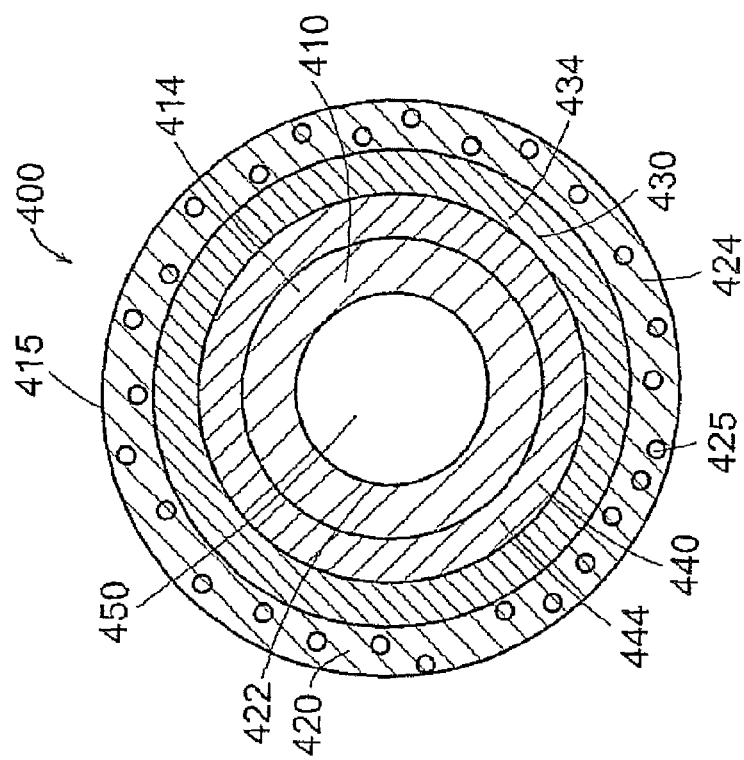
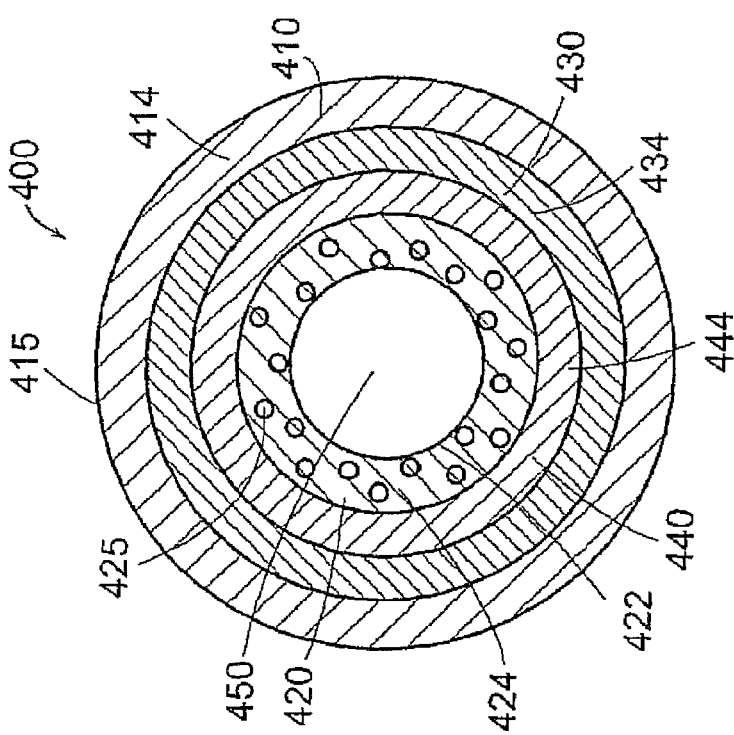
FIG. 4B
FIG. 4A

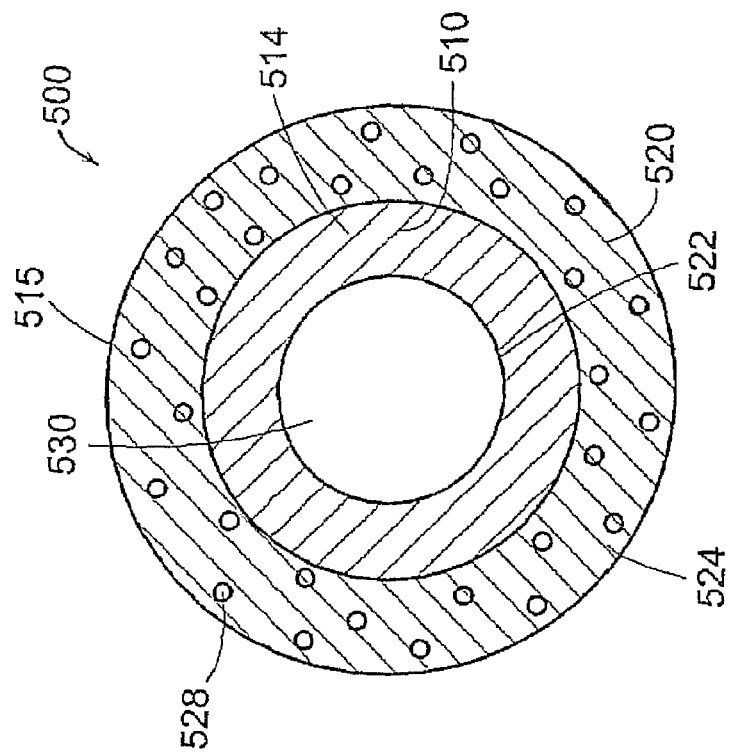
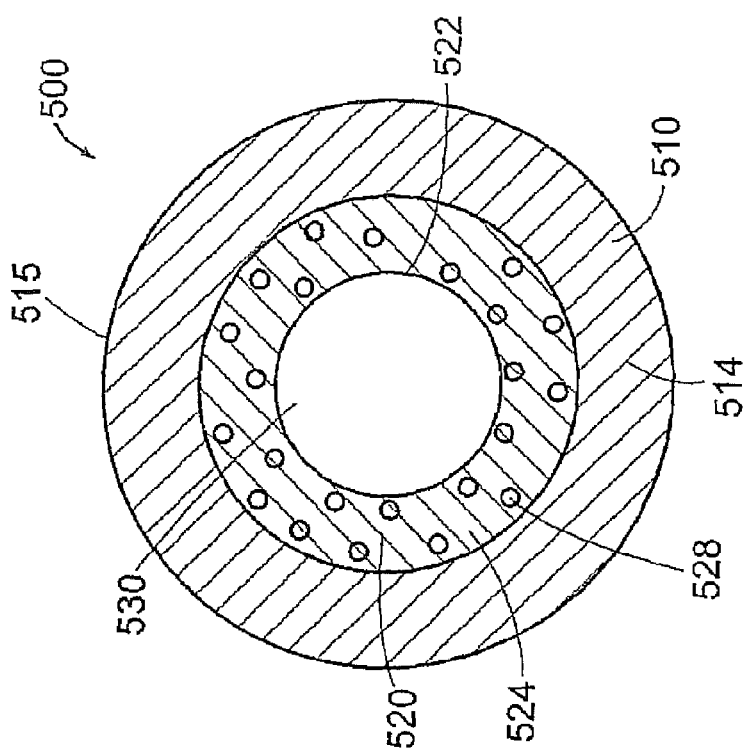

RESORPTION-CONTROLLABLE MEDICAL IMPLANTS

STATEMENT OF RELATED APPLICATIONS

This is a continuation of U.S. patent application Ser. No. 11/897,016, filed Aug. 28, 2007; which is a continuation of U.S. patent application Ser. No. 10/128,214, filed Apr. 23, 2002, entitled "Resorption-Controllable Medical Implants," now U.S. Pat. No. 7,261,734, all of which are incorporated by reference in their entirety herein.

TECHNICAL FIELD

This invention generally relates to medical implants. More particularly, the invention relates to resorption-controllable medical implants and methods for controlled resorption in the body of a mammal.

BACKGROUND INFORMATION

Medical implants have a variety of applications including kidney drainage and vascular surgery. Examples of medical implants include a ureteral stent used for drainage of urine from the kidney to the bladder and a vascular graft used for maintaining blood flow. Medical implants generally have to be removed from the body by an invasive procedure. Medical implants that are left in vivo may cause complications such as inflammation and other foreign body responses.

SUMMARY OF THE INVENTION

Medical implants with in vivo controllable resorption are therefore desired. In accordance with the invention, a medical implant is removed from a patient's body by non-invasive means, such as by degradation and resorption of the medical implant by natural biological mechanisms. Non-invasive removal of a medical implant avoids pain and suffering often associated with invasive or surgical procedures. In addition, a non-invasive removal procedure reduces medical expenses and lost productivity of the patient.

The present invention relates to devices and methods that are useful in controlling in vivo resorption of medical implants. Bioresorbable medical implants are designed to have differing resorption rates over time or over the topography of the implants.

An objective of this invention is to provide a medical implant that can be removed from the body of a mammal after the desired period of in vivo placement by natural biological mechanisms, such as by resorption of the implant material followed by normal elimination in a body fluid such as urine or feces. By using natural biological mechanisms of elimination, patient discomfort and the risk of complications to the patient is minimized compared to invasive procedures, such as surgical or endoscopic procedures. Another objective of this invention is to provide procedures in which removal of an implant is non-invasive, controllable, and predictable. In one embodiment, the rate of removal of the implant is pre-selectable. Medical implants according to the invention can take various shapes and can include stents, catheters, cannulas, plugs, fillers, constrictors, sheets, bone anchors, plates, rods, seeds, and tubes, for example.

In one aspect, the invention generally features a medical implant for use in a mammal. In one embodiment, the medical implant includes a first layer and a second layer disposed relative to the first layer (e.g., adjacent the first layer). The first layer includes a first bioresorbable material and is substantially free from resorbable particles. The second layer includes a second bioresorbable material and resorbable particles of a first kind which are dispersed within the second bioresorbable material.

In another aspect, the invention generally features a method for manufacturing a medical implant. In one embodiment, the method includes the following steps: extruding through a die a first bioresorbable material to form a first layer, and extruding through the die a second bioresorbable material and resorbable particles of a first kind together to form a second layer disposed relative to the first layer (e.g., adjacent the first layer). The first layer includes the first bioresorbable material and is substantially free from resorbable particles. The second layer includes the second bioresorbable material and resorbable particles of a first kind that are dispersed within the second bioresorbable material.

In yet another aspect, the invention generally features a medical implant for use in a mammal. In one embodiment, the medical implant includes a first layer and a second layer disposed relative to the first layer (e.g., adjacent the first layer). The first layer includes a first bioresorbable material and is substantially free from resorbable particles. The second layer includes a second bioresorbable material and a first bioactive agent.

In yet another aspect, the invention generally features a method for controlled release of a bioactive agent within the body of a mammal. In one embodiment, the method includes the steps of providing a medical implant insertable into a mammal and contacting the medical implant with a body fluid of the mammal, thereby causing a controlled release of the bioactive agent. The medical implant includes a first layer and a second layer disposed relative to the first layer (e.g., adjacent the first layer). The first layer includes a first bioresorbable material and is substantially free from resorbable particles. The second layer includes a second bioresorbable material and a first bioactive agent.

These and other features, aspects, and advantages will become more apparent from the following description, drawings, and claims.

BRIEF DESCRIPTION OF THE DRAWINGS

The drawings are not necessarily to scale, emphasis instead generally being placed upon illustrating the principles of the invention.

FIG. 4a is a cross-sectional schematic view of an embodiment of a four-layered tubular medical implant according to the invention.

FIG. 4b is a cross-sectional schematic view of an embodiment of a four-layered tubular medical implant according to the invention.

FIG. 5a is a cross-sectional schematic view of an embodiment of a tubular medical implant according to the invention including a bioactive agent.

FIG. 5b is a cross-sectional schematic view of an embodiment of a tubular medical implant according to the invention including a bioactive agent.

DESCRIPTION

Figure 1A:
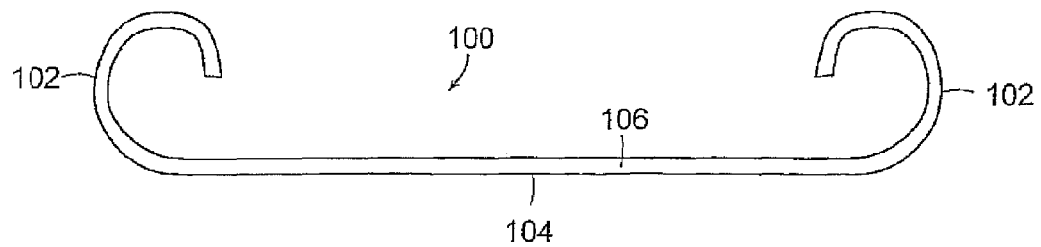
FIGS. 1a-1i show some exemplary embodiments of medical implants according to the invention which include a stent (FIG. 1a), a seed (FIG. 1b), a cannula (FIG. 1c), a bone anchor (FIG. 1d), a sheet (FIG. 1e), a plate (FIG. 1f), a rod (FIG. 1g), a plug (FIG. 1h), and a constrictor (FIG. 1i).

In general, the bioresorbable hydrogels forming the bulk component of medical implants are permeable to certain body fluids including water and small ionizable molecules dissolved therein. A body fluid is capable of penetrating the matrix of the implant material through various mechanisms (e.g., diffusion, migration, or capillary action). One way to control resorption in medical implants is to control the degree of porosity and thus the diffusion rate of a fluid in the implant material. The porosity of the implant material may be created or controlled by embedding, in a bulk bioresorbable material, resorbable particles that resorb at a different rate than the bulk bioresorbable material. Another way to control resorption of the implant is to have two or more layers of bioresorbable bulk materials with or without various amounts of embedded resorbable particles. In combination, controlling resorption therefore can be achieved by controlling the speed of penetration of the body fluid through a medical implant having various amounts of resorbable particles in its various layers.

In one aspect, the invention generally features a medical implant having a resorption profile that include one or more resorption rates for use in a mammal. In one embodiment according to the invention, an implant includes two layers of bioresorbable material having differing compositions. The first layer of the medical implant includes a first bioresorbable material. The first layer is substantially free from resorbable particles. As used herein, "substantially free from resorbable particles" means that the volume percentage of resorbable particles in the respective layer is less than about 5%, more preferably less than about 3%, and most preferably less than about 1%. The first layer may form the interior surface of a hollow medical implant having two or more layers and having an interior surface and an exterior surface. The first layer may also form the exterior surface of a medical implant having two or more layers.

The second layer is disposed relative to the first layer and includes a second bioresorbable material and resorbable particles of a first kind. The resorbable particles are dispersed within the second bioresorbable material. The second layer can be the interior layer forming the interior surface of a medical implant with two or more layers and having an interior surface and an exterior surface. The second layer can be one of the middle layers (i.e., not forming either the interior surface or the exterior surface) of a medical implant with more than two layers. The second layer can also be the exterior layer forming the exterior surface of a medical implant with two or more layers. In some embodiments, the second layer is disposed adjacent the first layer.

The thickness of each of the first, the second, and any additional layers can range from about 1 micron to about 2.5 cm. In other embodiments, the thickness of each of the first, the second, and any additional layers range from about 1 micron to about 10 microns, from about 10 microns to about 100 microns, from about 100 microns to about 1 mm, from about 1 mm to about 1 cm, and from about 1 cm inch to about 2.5 cm. Each of the layers can have a different thickness. In addition, the thickness of each layer may not be uniform longitudinally, laterally, or radially although uniformity may be preferred. The thickness of a layer can be designed to achieve the desired resorption rate.

The bioresorbable material of the various layers can form the bulk of the respective layer. The bioresorbable material can be a reversibly ionically crosslinked polymeric material, which can include an ionically crosslinkable polymer and crosslinking ions. The ionically crosslinkable polymer can be anionic or cationic and may include, but is not limited to, at least one polymer or copolymer such as polyacrylic acids, polymethacrylic acid, polyethylene amine, polysaccharides, alginic acid, pectinic acid, carboxymethylcellulose, hyaluronic acid, heparin, chitosan, carboxymethyl chitosan, carboxymethyl starch, carboxymethyl dextran, heparin sulfate, chondroitin sulfate, cationic starch, and salts thereof. Illustrative examples of cationic crosslinking ions include polycations such as calcium, magnesium, barium, strontium, boron, beryllium, aluminum, iron, copper, cobalt, lead, and silver ions. Illustrative examples of anionic crosslinking ions include polyanions such as phosphate, citrate, borate, succinate, maleate, adipate, ethylene diamine tetraacetate (EDTA), and oxalate ions, and, more broadly, anions derived from polybasic organic or inorganic acids. In one embodiment, the crosslinking cations are barium, and the crosslinking anions are phosphates. The bioresorbable material may also be a reversibly covalently crosslinked polymeric material.

The bioresorbable materials can be a hydrogel having a water content of less than about 90% by weight and possessing sufficient mechanical strength to serve as, for example, a stent, a catheter, a cannula, a plug, a constrictor, a sheet, a filler, a bone anchor, a plate, a rod, a seed, a tube, or a portion thereof. As used herein, the term "hydrogel" indicates a material that is water permeable, yet water insoluble in its crosslinked form, but would release water-soluble components upon removal of the crosslinks. A device may be in its hydrogel form or in a dehydrated form.

As used herein, a soluble material is a material that has a water solubility such that upon exposure to a body fluid an amount of the material will dissolve or erode over time. "Body fluid" refers to fluids in the body of a mammal including, but not limited to, blood, urine, saliva, lymph, plasma, gastric, biliary, or intestinal fluids, seminal fluids, and mucosal fluids or humors. A degradable material is a material that can decompose, degenerate, degrade, depolymerize, or otherwise reduce the molecular weight of the starting compound(s) such that the resulting compound(s) is soluble in water or, if insoluble, can be suspended in a body fluid and transported away from the implantation site without clogging the flow of the body fluid. A resorbable material is a material that is soluble, degradable as defined above, or is an aggregate of soluble and/or degradable material(s) with insoluble material(s) such that, with the resorption of the soluble and/or degradable materials, the residual insoluble materials are of sufficiently fine size such that they can be suspended in a body fluid and transported away from the implantation site without clogging the flow of the body fluid. Ultimately, the materials are eliminated from the body either by excretion in perspiration, urine or feces, or dissolved, degraded, corroded or otherwise metabolized into soluble components that are then excreted from the body. A bioresorbable material is a resorbable material that is biocompatible. A biocompatible material is a material that is compatible with living tissue or a living system, non-toxic or non-injurious, and does not cause immunological reaction or rejection.

Generally, to increase the resorption rate of a medical implant, particles with higher resorption rate can be embedded in the bioresorbable bulk material of which the medical implant is made to facilitate the resorption of the bioresorbable bulk material upon its contact with a body fluid. The faster resorption rate of the bulk medical implant is achieved due to the increased surface area created by the particles. Also generally, to decrease the resorption rate of a medial implant or delay the initiation of resorption, less or no particles are embedded in the bioresorbable material. In addition, several layers that include bioresorbable material, but are substantially free from resorbable particles, can be added to slow down or delay resorption of a medical implant. Thus, resorption rates in the medical implant can be controlled by varying the chemical and physical properties of the bioresorbable materials composing the layers in the implant, the number of layers of the bioresorbable materials alone, the presence or absence of particles embedded in the layers, and if particles are present, the particles size, shape, amount, distribution, and most importantly, its resorption rate, etc.

The particles may be resorbable or have magnetic properties. The resorbable particles can include a swelling agent, a hydrolysable agent, or a soluble agent, or a combination thereof. These agents may be organic compounds, polymeric compounds, soluble or degradable inorganic compounds, and/or organic or inorganic crystals or powder aggregates. The particles may also include a polymeric material, e.g., polysaccharides, polyglycolic acid, polylactic acid, cellulose derivatives, hyaluronic acid, polylactams, hydrogels or other colloid. The particles can be resorbable particles having magnetic properties. The resorption rate of the particles can be controlled by its size, shape, composition, etc.

The size of the embedded particles, when present, can be from about 5 nm to about 1 mm depending on the type of the implant. In some applications, the preferred size can vary from about 5 nm to about 1 µm. In other applications, the preferred size can vary from about 1 µm to about 100 µm, from about 100 µm to about 500 µm, or from about 500 µm to about 1 mm. There is no requirement that all the particles be of the same size.

The distribution of the particles, when present in the bioresorbable material, need not be uniform and should be based on the desired resorption profile. A resorption profile refers to both temporal and topographical variations of the implant resorption rates. A resorption profile can have a plurality of varying resorption rates. The resorption profile can be a function of time such as two or more differing sequential rates (e.g., slow initial resorption and fast late-stage resorption, or vice versa). The resorption profile can also be a function of a physical dimension of the implant (e.g., slow resorption of one portion and fast resorption of another portion). For example, concentration of embedded particles may be higher in the pigtail region of a ureteral stent to favor faster dissolution and quicker removal of the stent from the ureter. Temporal or topographical uniformity of the resorption profile may be preferred in certain circumstances.

The volume percentage of the particles in the bioresorbable material can be equal to or less than about 50 weight percent. In some embodiments, the volume percentage is less than about 1% or greater, up to about 50 weight percent.

The particles can be made of the same types of polymeric material as the bioresorbable material but with substantially different characteristics such that their resorption occurs at a different rate, generally faster than the resorption of the bioresorbable material. Those characteristics can be controlled through molecular weight, crosslinking ratio (e.g., the number of crosslinks per crosslinkable sites or the number of crosslinks per unit volume or weight of the material), or different crosslinking ions (e.g. ions of a weaker electronic affinity). Characteristics of the polymeric material can be modulated by modifying factors such as these to suit the specific application at hand.

The period for substantial resorption of a medical implant ranges from about 1 to about 28 days. As used herein, "substantial resorption" refers to a stage of resorption where the medical implant has corroded, fragmented, disintegrated, degraded, or dissolved to such a degree that it has lost its intended mechanical function. In one embodiment, the period for substantial resorption of a medical implant ranges from about 1 to about 2 days. In another embodiment, the period for substantial resorption of a medical implant ranges from about 2 to about 7 days. In another embodiment, the period for substantial resorption of a medical implant ranges from about 7 to about 14 days. In another embodiment, the period for substantial resorption of a medical implant ranges from about 14 to about 28 days.

Illustrative examples of medical implants of the invention include stents, catheters, cannulas, plugs, fillers, constrictors, sheets, bone anchors, plates, rods, seeds, tubes, or portions thereof. Exemplary medical devices according to the invention are shown in FIGS. 1*a-i*. Devices according to the invention can take many shapes or configurations other than those depicted in FIGS. 1*a-i*, as these are only examples and are not intended to encompass all the embodiments of the invention. Depending on the application, the entire device or one or more portions of the device can be made of the bioresorbable compositions of the present invention.

FIG. 1*a* depicts a tubular stent 100 that includes two coil-shaped end portions 102, a central portion 104, a lumen or passageway 106 within the tube from one end to the other. Stents can be used for maintaining the patency of a body vessel such as, for example, urinary drainage from the kidney to the bladder in patients with uretertal obstruction or injury, or to protect the integrity of the ureter in a variety of surgical manipulations. The device can be extruded or molded with the bioresorbable composition of this invention such that the entire device is made thereof or such that only one or more portions of the device include the compositions of the invention, such as one or both end portions 102, for example.

Figure 1B:
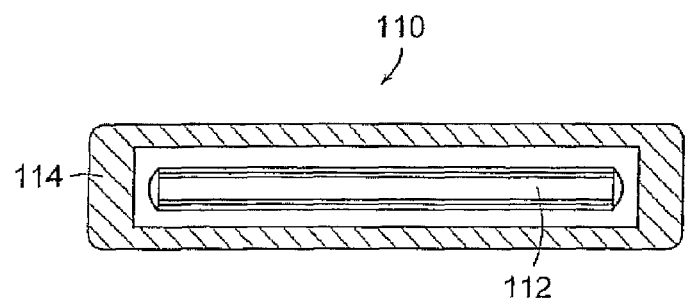

FIG. 1*b* depicts a seed 110 shaped into an elongated pellet that includes an active substrate 112 (such as a medicine) within a shell or coating 114 made according to the invention. Alternatively, the medicine can be mixed throughout the seed, and the shape of the seed can be accommodated for the intended use into other shapes, such as spherical, egg-shape, for example. Such seeds can be used for delivering medicine to a specific organ such as in prostate hyperplasia and to provide control release of the medicine into the organ upon resorption of the seed. See also, U.S. Pat. No. 4,697,575 (incorporated herein by reference in its entirety). The entire device may be made according to the invention with the medicine embedded therein that is introduced during manufacture. Alternatively, only the shell or coating 114 may be made according to the invention.

Figure 1C:
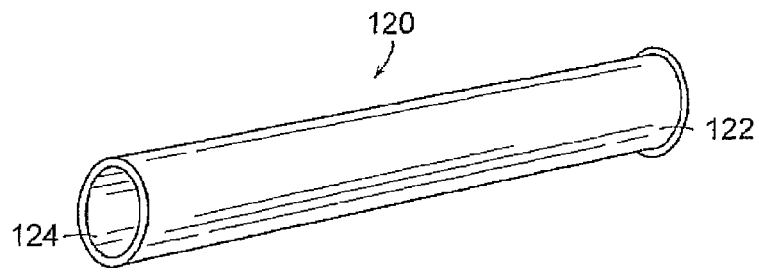

FIG. 1c depicts a cannula 120 that includes a tube 122 and a lumen or passageway 124. Cannulas are generally used to gain access to an organ or vessel in a body percutaneously or through a natural body opening. Similarly to a cannula, a catheter is an elongated tube for insertion percutaneously or through a natural body opening into a body cavity, duct, or vessel to allow the passage of a fluid or distend a passageway. Catheters are generally used for the drainage of urine from the bladder through the urethra, for insertion into a blood vessel for diagnostic purposes, or to drain an abscessed area. The entire device or only a portion of a cannula or catheter, such as one or both end portions 122 or a middle section therebetween for example, may be extruded or molded according to this invention.

Figure 1D:
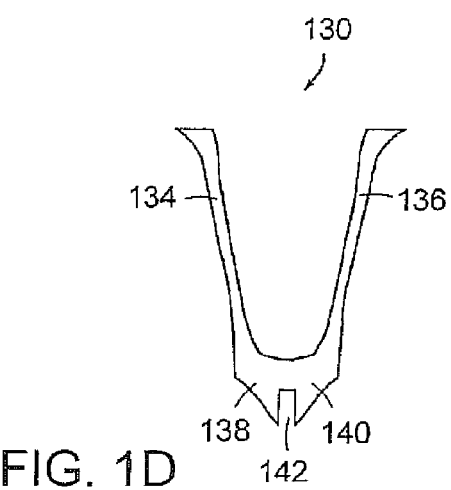

FIG. 1d depicts a bone anchor 130 that includes anchoring legs 134, 136 which include distal portions 138, 140, respectively, in the form of tapered cones separated by a slot 142. See U.S. Pat. No. 6,146,406 (incorporated herein by reference in its entirety). Bone anchors are commonly used to attach soft tissue to bone, e.g., during rotator cuff ligament reconstruction. An anchor having an attached suture can be placed into a bone hole. The suture can then be used to attach soft tissue to the bone. It is beneficial to have the entire bone anchor or one or more portions, e.g., a portion of or the entire of one or both legs 134 and 136, made according to the invention. After secure attachment of the soft tissue and the suture, the implanted bone anchor will then resorb over time without the need for surgical removal.

Figure 1E:
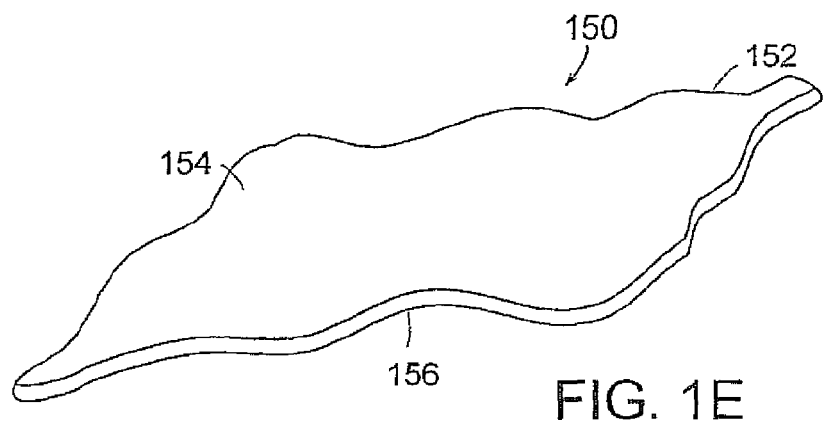

FIG. 1e depicts a sheet 150 that includes a flexible and flat member 152, a top surface 154 and bottom surface 156. For example, a sheet can be used as anti-adhesion barrier to isolate tissues or organs such that they do not adhere to the organ or tissue. The entire sheet or only one or more portions of the sheet, such as one or both surfaces 154 and 156, may be made according to this invention.

Figure 1F:
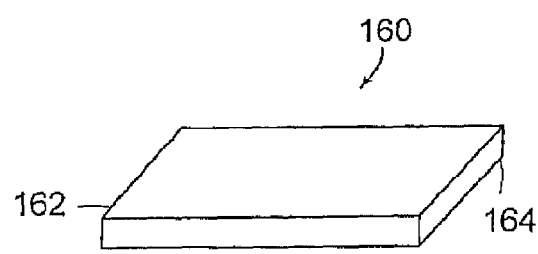

Similarly, as depicted in FIG. 1f, a plate 160 includes a flat member 162 that is typically rigid. For example, a plate can be used as an organ support or as a space filler. The entire plate or only one or more portions of the plate, such as one or all corners 164, may be made according to this invention.

Figure 1G:
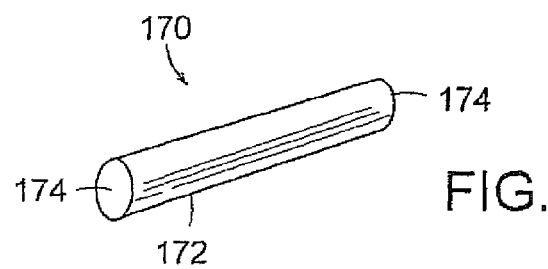

As depicted in FIG. 1g, a rod 170 includes an elongated member 172 and end portions 174. A rod or only one or more portions of the rod, such as one or both end portions 174 or a portion therebetween, may be made according to this invention. For example, a plate can be used as an organ support or as a space filler.

Figure 1H:
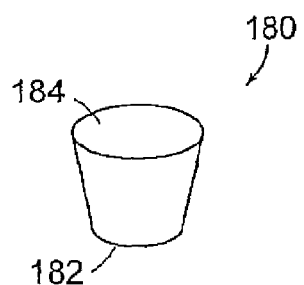

FIG. 1h depicts a plug 180 having a proximal end portion 182 and a distal end portion 184 that is usually used to stop fluid flow. A plug may or may not be formed in situ. The entire plug or only one or more portions of the plug, such as one or both end portions 182 and 184, may be made according to this invention.

Figure 1I:
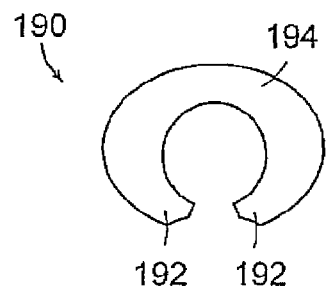

FIG. 1i depicts a constrictor 190 that includes arms 192 and a body portion 194. A constrictor can be used to control the location of a body part or to prevent aneurysms. The entire constrictor or only one or more portions of the constrictor, such as one or both arm portions 192, may be made according to this invention.

Figure 2A:
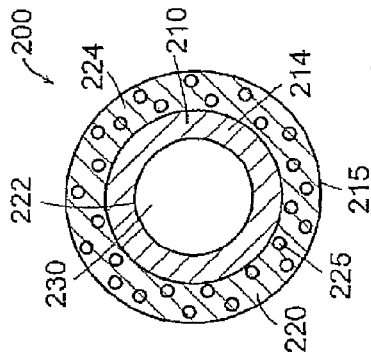
FIG. 2a is a cross-sectional schematic view of an embodiment of a two-layered tubular medical implant according to the invention.

Referring to FIG. 2a, which is a cross-sectional view of a tubular medical implant 200 such as a stent, the implant 200 is fabricated to include two layers. The tubular medical implant 200 includes a first layer 210 forming the exterior surface 215 of the implant and a second layer 220 forming the interior surface 222 of the implant and defining a lumen 230. Conversely, in FIG. 2b, the tubular medical implant 200 includes a first layer 210 forming the interior surface 222 of the implant and defining a lumen 230 and a second layer 220 forming the exterior surface 215 of the implant.

In both of these embodiments, the first layer 210 includes a first bioresorbable material 214. The first layer 210 is substantially free from resorbable particles. The second layer 220 is disposed adjacent the first layer 210 and includes a second bioresorbable material 224 and resorbable particles of a first kind 225. The bioresorbable materials 210 and 220 of the first and second layers may be identical or different.

Figure 2B:
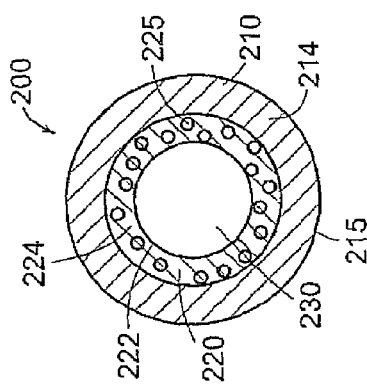
FIG. 2b is a cross-sectional schematic view of an embodiment of a two-layered tubular medical implant according to the invention.

Comparing the embodiments shown in FIGS. 2a and 2b, the one in FIG. 2a retains its exterior diameter longer than the one in FIG. 2b (assuming the embedded particles 225 resorb faster than the bioresorbable material 220). Therefore, a two-layered medical implant can be constructed to achieve a desired resorption profile through variation of the bioresorbable materials used, the thickness of the layers, and the use or placement of embedded particles.

Figure 3A:
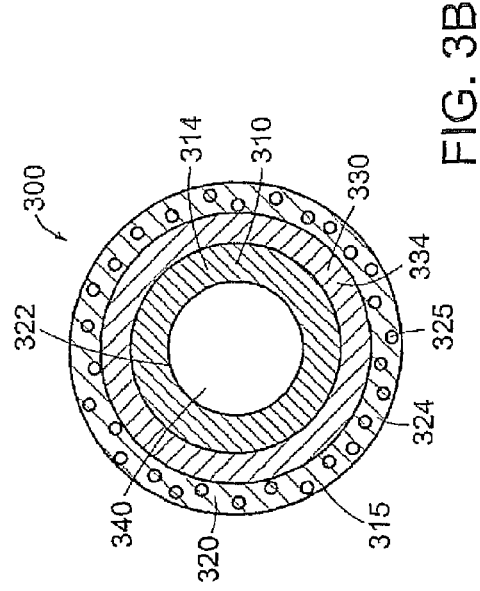
FIG. 3a is a cross-sectional schematic view of an embodiment of a three-layered tubular medical implant according to the invention.

Referring to FIG. 3a, which is a cross-sectional view of a tubular medical implant 300 such as a stent, the implant 300 is fabricated to include three layers. The tubular medical implant 300 includes a first layer 310 forming the exterior surface 315 of the implant, a second layer 320 forming the interior surface 322 of the implant and defining a lumen 340, and a third layer 330 (the middle layer), which is disposed adjacent the second layer. Conversely, in FIG. 3b, the tubular medical implant 300 includes a first layer 310 forming the interior surface 322 of the implant and defining a lumen 340, a second layer 320 forming the exterior surface 315 of the implant, and a third layer 330 (the middle layer).

The first layer 310 includes a first bioresorbable material 314. The first layer is substantially free from resorbable particles. The second layer 320 includes a second bioresorbable material 324 and resorbable particles of the first kind 325. In one embodiment, the first and second bioresorbable materials 314 and 324 are identical. A third layer 330 is placed adjacent the second layer 320 and includes a third bioresorbable material 334 and optionally resorbable particles of a second kind (not shown). The resorbable particles of a second kind can be dispersed in the third bioresorbable material 334. In another embodiment, the third layer 330 includes a third bioresorbable material 334. All three bioresorbable materials may be identical or different. The bioresorbable materials from the various layers may be identical in kind but different in properties such as resorption rate, permeability rate, diffusion rate, density and stiffness. The resorbable particles of the first kind and resorbable particles of the second kind may also be identical in kind or different. The resorbable particles embedded in the various layers may be identical in kind but different in properties such as resorption rate, permeability rate, diffusion rate, size, shape, density, amount, stiffness and distribution.

Figure 3B:
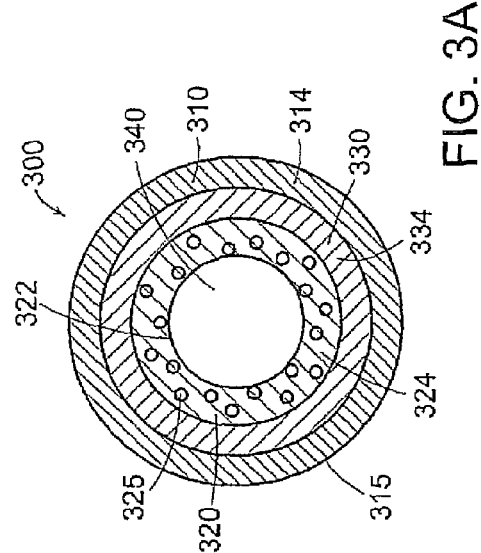
FIG. 3b is a cross-sectional schematic view of an embodiment of a three-layered tubular medical implant according to the invention.

Thus, the embodiments shown in FIGS. 3a-b allow additional fine-tuning of the resorption of the medical implant, thereby achieving the desired resorption profile. A variety of resorption profiles can be designed according to this invention by adding layers to the implant or by adding particles to the layers and arranging the sequence of the layers within the implant or the topography and concentration of the particles within each layer. For example, the resorption profile can be designed to provide slow initial resorption with accelerated middle-stage resorption but slowed late-stage resorption.

Referring to FIG. 4a, which is a cross-sectional view of a tubular medical implant 400 such as a stent, the implant 400 is fabricated to include four layers. The tubular medical implant 400 includes a first layer 410 forming the exterior surface 415 of the implant, a second layer 420 forming the interior surface 422 of the implant and defining a lumen 450, a third layer 430 (one of the middle layers) disposed adjacent the first layer 410, and a fourth layer 440 (the other one of the middle layers) disposed adjacent the second layer 420. Conversely, in FIG. 4b, the tubular medical implant 400 includes a first layer 410 forming the interior surface 422 of the implant and defining a lumen 450, a second layer 420 forming the exterior surface 415 of the implant, a third layer 430 (one of the middle layers) disposed adjacent the second layer 420, and a fourth layer 440 (the other one of the middle layers) disposed adjacent the first layer 410.

The first layer 410 includes a first bioresorbable material 414. The first layer is substantially free from resorbable particles. The second layer 420 includes a second bioresorbable material 424 and resorbable particles of the first kind 425. The third layer 430 includes a third bioresorbable material 434. The fourth layer 440 includes a fourth bioresorbable material 444. The third layer 430 can further include resorbable particles of the second kind (not shown). The fourth layer 440 can further include resorbable particles of the third kind (not shown). The first, second, third, and fourth bioresorbable materials can be identical or different. The first, second, and third resorbable particles may also be the same or different.

The medical implant can include one or more additional layers, allowing further fine-tuning of the resorption rate and time profile of the medical implant. Each of the additional layers includes a bioresorbable material. At least one of the additional layers further includes resorbable particles of a fourth kind dispersed within the bioresorbable material. In one embodiment, each of the additional layers includes a bioresorbable material and resorbable particles of a fourth kind. The bioresorbable materials of each of the additional layers may be identical. All resorbable particles may be identical in kind or different.

In another aspect, the invention generally features methods for manufacturing a medical implant. In one embodiment, the method include the steps of: extruding through a die a first bioresorbable material to form a first layer, and extruding through the die a second bioresorbable material and resorbable particles of a first kind to form a second layer disposed relative to the first layer. The first layer includes the first bioresorbable material and is substantially free from resorbable particles. The second layer includes the second bioresorbable material and resorbable particles of a first kind dispersed within the second bioresorbable material. The second layer can be extruded adjacent the first layer.

In one embodiment, the two extruding steps occur simultaneously. In another embodiment, the above method further includes the step of crosslinking the first bioresorbable material and the step of crosslinking the second bioresorbable material. The steps of crosslinking the first and second materials may occur simultaneously or sequentially depending on the application. The method can further include extruding the medical implant through the die with a bioresorbable material one or more times to form a third or more additional layers. The third and each of the additional layers, if any, include a bioresorbable material. One or more of these layers may further include resorbable particles that are identical or different from those embedded in the second layer.

In yet another aspect, the invention generally features a medical implant for delivering a bioactive agent into the body of a mammal. The bioactive agent can be dissolved in the mixture of the bioresorbable material or dispersed as particles. The medical implant includes a first layer and a second layer. The first layer includes a first bioresorbable material. The first layer is substantially free from resorbable particles. The second layer is disposed relative to the first layer (e.g., adjacent the first layer) and includes a second bioresorbable material and a first bioactive agent.

As discussed above, such bioactive agents include, but are not limited to, anti-inflammatory agents, antimicrobials such as antibiotics or antifungal agents, anti-viral agents, anti-infective agents, tissue growth promoters, immunosuppressants, and anti-adhesion agents, radiopaque and contrasting agents, and bioadhesives. Illustrative examples of anti-inflammatory agents include, but are not limited to, glucocorticoids such as hydrocortisone and prednisolone. Illustrative examples of antimicrobial agents include, but are not limited to, triclosan, aminoglycosides, trimethoprim, sulfamethoxazole, nitrofurantoin, quinolones (e.g., ofloxacin, norfloxacin, ciprofloxacin, trovafloxin), ampicillin, and amoxicillin. Illustrative examples of anti-viral agents include, but are not limited to, ribavirin and respigam. Illustrative examples of tissue growth promoters include, but are not limited to, prolactin. Illustrative examples of immunosupressants include, but are not limited to, azathiopurine, 6-mercaptopurine, and cyclosporine A. Illustrative examples of radiopaque agents in liquid or solid form include, but are not limited to, tantalum powder, platinum powder, barium sulfate, bismuth subcarbonate, ionic or non-ionic contrasting agents such as diatrizoates, iodipamide, iohexol, iopamidol, iothalamate, ioversol, ioxaglate, and metrizamide. Examples of liquid contrasting agents include, but are not limited to, Omnipaque®, Visipaque® manufactured by Nycomed Amersham Imaging of Princeton, N.J., or RenoCal® manufactured by Bracco Diagnostic Inc. of Princeton, N.J. Illustrative bioadhesive agents include, but are not limited to, collagen, laminin, fibronectin, poly-D-lysine, poly-L-lysine, decapeptides.

Referring to FIGS. 5a-b, a medical implant 500 can be constructed for a controlled delivery of a pre-selected bioactive agent to a location within the body of a mammal. In one embodiment, the medical implant 500 includes a first layer 510, a second layer 520, and a lumen 530. The first layer 510 includes a first bioresorbable material 514. The first layer is substantially free from resorbable particles. The second layer 520 is disposed adjacent the first layer and includes a second bioresorbable material 524 and a first bioactive agent 528. The bioactive agent 528 can be dispersed into the second bioresorbable material 524 in the form of particles as shown in FIGS. 5a-b. The bioactive agent 528 can also be dissolved within the matrix of the second bioresorbable material 524. The bioactive agent 528 diffuses out of the second bioresorbable material 524 upon contacting a body fluid by the second bioresorbable material 524.

In FIG. 5a, the first layer 510 that includes the first bioresorbable material 514 forms the exterior surface 515 of the implant. Conversely, in FIG. 5b, the first layer 510 that includes the first bioresorbable material 514 forms the interior surface 522 and defines a lumen 530.

Figure 6B:
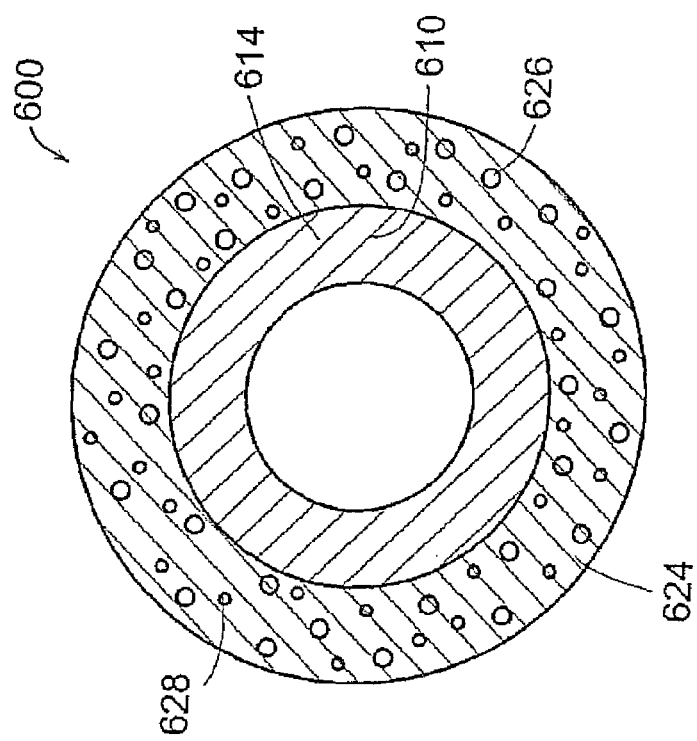
FIG. 6b is a cross-sectional schematic view of an embodiment of a tubular medical implant according to the invention including a bioactive agent.
Figure 6A:
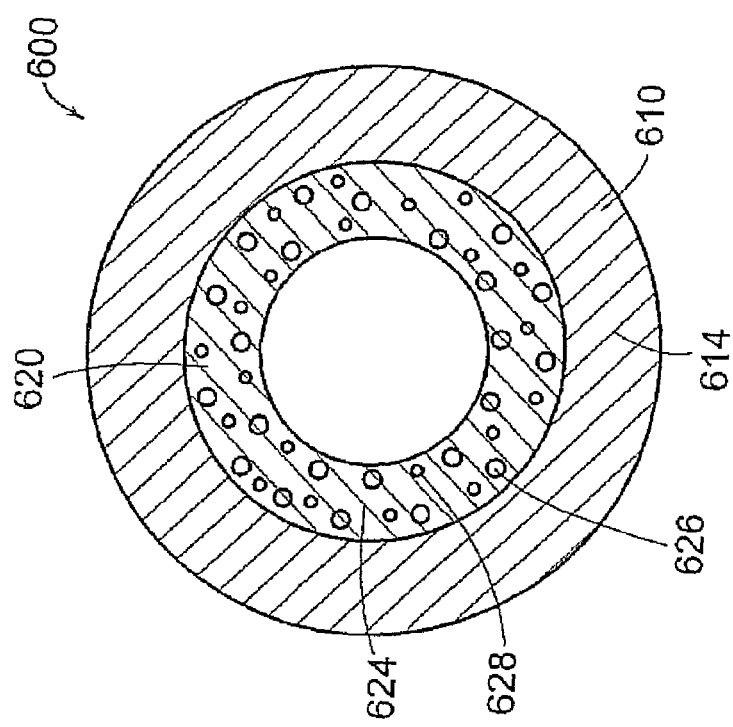
FIG. 6a is a cross-sectional schematic view of an embodiment of a tubular medical implant according to the invention including a bioactive agent.

In FIGS. 6a-b, which are otherwise identical to FIGS. 5a-b, the second layers of the implant 600 further include resorbable particles 626. The medical implants 500 and 600 can further include one or more additional layers disposed relative to the first and second layers (e.g., between the first and second layers).

The bioactive agent loading can generally be from about 0.01 weight percent to about 40 weight percent depending on the agent and the need of the treatment. Such bioactive agents include but are not limited to antibiotics, anti-adhesion agents, anti-inflammatory agents, anti-microbials, anti-infective agents, tissue growth promoters, and bioadhesives.

The medical implant may be manufactured and used in conjunction with a delivery device that provides the necessary mechanical support or facilitate the insertion/retraction.

Compositions of the materials used to construct the above medical implants can be produced by any conventional ways of forming a mixture with two or more components. The compositions may be prepared by mixing precursor components followed by a chemical processing of either the resorbable particles or the bioresorbable material. For example, a conventional mechanical mixer may be sufficient to produce a composition having particles of desired properties and a bioresorbable material. A solvent such as water may be used so that a solution of the bioresorbable material is mixed with the particles followed by removal of the solvent. Such methods include first mixing precursor(s) of the bioresorbable material with the particles followed by a reaction of the precursor(s) to produce the bioresorbable material. Also, one can first mix precursor(s) of the particles with the bioresorbable material followed by a reaction of the precursor(s) to produce the desired particles. Chemical modifications that may be used in preparing the compositions of the invention include, but are not limited to, polymerization, crosslinking reactions either ionic or covalent so as to gel, cure, or set a precursor polymer.

The implants (or components of the implants) of the present invention may be made via various manufacturing processes including extrusion, injection molding, solution dipping, rotational molding, compression, roll wrapping, etc.

The devices of the present invention can be used for any treatment involving a medical implant that needs a controlled resorption rate. For example, a ureteral stent made with the compositions of the present invention can be placed in a patient. The stent will then resorb at a rate dependent on the composition of the material. The stent can be set to resorb quickly or slowly by pre-selecting its composition as described earlier.

In yet another aspect, the invention generally features a method for a controlled release of a bioactive agent within the body of a mammal. In one embodiment, the method includes the steps of providing a medical implant insertable into the body of a mammal and contacting the medical implant with a body fluid, thereby causing a controlled release of the bioactive agent. The medical implant includes a first layer and a second layer. The first layer includes a first bioresorbable material. The first layer is substantially free from resorbable particles. The second layer is disposed relative to the first layer (e.g., adjacent the first layer) and includes a second bioresorbable material and a first bioactive agent.

In one embodiment, the method includes a step of inserting a medical implant into the body of a mammal. Insertion of the medical implant may be assisted with or preceded by the use of an endoscope, a cannula, a pusher, a guide wire, a dilator depending on the nature and final location of the implant. The medical implant can be a stent, a catheter, a cannula, a plug, a constrictor, a sheet, a filler, a bone anchor, a plate, a rod, a seed, a tube, or a portion thereof.

EXAMPLE 1

A paste containing 17% by weight of sodium alginate was prepared by adding 20.5 grams of sodium alginate into 100 grams of de-ionized water at 30.degree. C. This paste was labeled Paste I (pure alginate paste). A pre-determined amount of radiopacifier particles of bismuth subcarbonate was added to and mixed with a portion of Paste I to reach a radiopacifier particle concentration of 7% by weight. This paste was labeled Paste II (particle embedded alginate paste).

Paste I and Paste II were filled in two separate syringes. Each of Paste I and Paste II was separately extruded to produce one tube (Tube I) from Paste I (pure alginate paste) and one tube (Tube II) from Paste II (particles embedded alginate paste). Each of Tube I and Tube II was separately extruded directly into a bath containing a calcium chloride solution (20% by weight). Tube I and Tube II had the same diameters of about 3 mm and the same wall thickness of about 0.5 mm. After about one hour in the bath, each tube was washed with de-ionized water.

Figure 7:
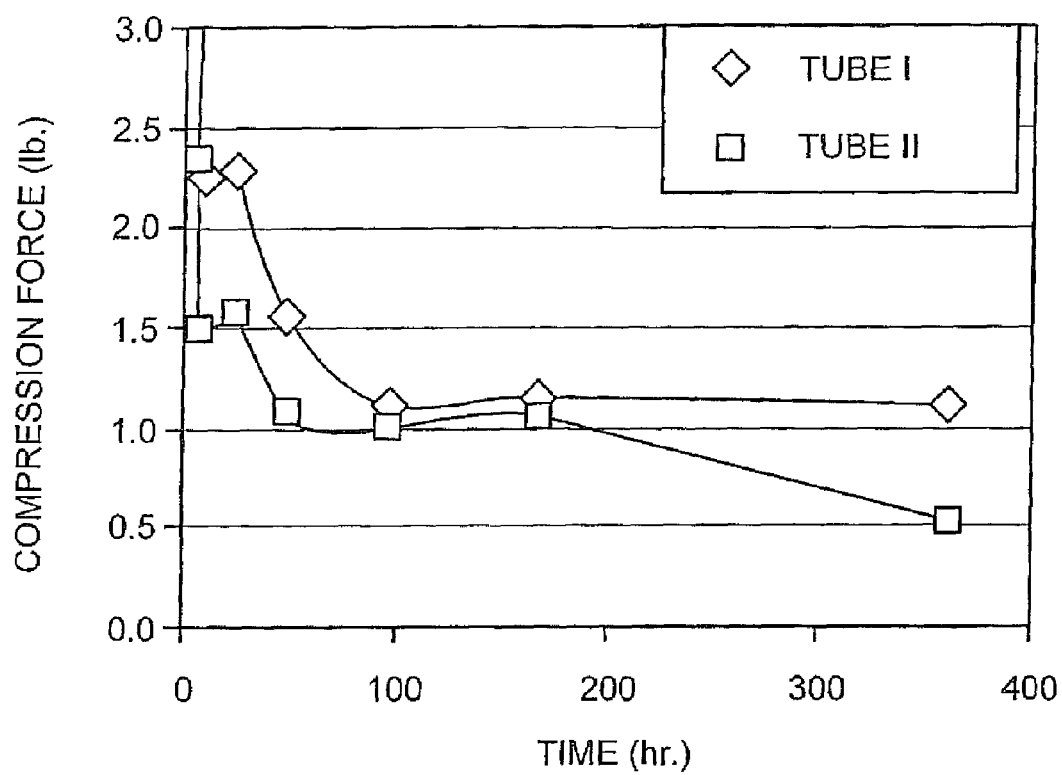
FIG. 7 shows a comparison of the compression forces measured on a tube made of pure alginate and a tube made of alginate mixed with radiopacifier particles.

Each tube was cut into sections of 2 cm long and incubated in an artificial urine, which was a simulated urine with compositions given in Table 1 below. Sulfate and phosphate ions in the solution have the tendency to combine with the calcium ions, which functions as crosslinker in the tubes, to form insoluble salts. The stripping of the crosslinking ions decreases the mechanical properties of the tube. The compression force required to collapse a tube is one of several key mechanical properties of a tube. Compression forces were measured for both tubes and are presented in Table 2 below. FIG. 7 is a graphical presentation of the data in Table 2, which demonstrates that when incubated in artificial urine Tube I (pure alginate) loses its mechanical strength at a significantly slower rate than Tube II (particle-embedded alginate). This in-turn demonstrates that the pure alginate tube has a significantly slower dissolution rate than the tube made of particle-embedded alginate.

TABLE 1

Composition of Artificial Urine

| Component | Grams | Wt % | Molarity | Molarity | Mmol/L | Mg/dL |
|---|---|---|---|---|---|---|
| Urea | 19.4 | 1.94 | 3.33E−01 Urea | 3.33E−01 | 333.3 | 2000 |
| NaCl | 8 | 0.80 | 1.41E−01 Na | 1.77E−01 | 176.8 | 406.6 |
| $MgSo_4 * 7H_2O$ | 1.1 | 0.11 | 4.61E−03 Cl | 1.45E−01 | 145.1 | 522.5 |
| $Na_2SO_4$ | 1.5 | 0.15 | 1.09E−02 $SO_4$ | 1.55E−02 | 15.5 | 148.9 |
| $KH_2PO4$ | .91 | 0.09 | 6.85E−03 $PO_4$ | 1.37E−02 | 13.7 | 130.0 |
| $Na_2HPO4$ | .94 | 0.09 | 6.83E−03 Ca | 1.90E−03 | 1.9 | 7.6 |
| $CaCl_2 * 2H_2O$ | .27 | 0.03 | 1.90E−03 Mg | 4.61E−03 | 4.6 | 11.2 |
| DI Water | 969.25 | 96.79 | 5.56E+01 K | 6.85E−03 | 6.9 | 26.7 |

TABLE 2

Compression Force after Dissolution in Artificial Urine

| Time in Artificial urine (hr) | Tube I (lb.) | Tube II (lb.) |
|---|---|---|
| 4 | 7.586 | 2.346 |
| 8 | 2.262 | 1.489 |
| 24 | 2.289 | 1.569 |
| 48 | 1.561 | 1.072 |
| 96 | 1.123 | 0.997 |
| 168 | 1.160 | 1.055 |
| 360 | 1.123 | 0.519 |

EXAMPLE 2

Paste I and Paste II as prepared in Example 1 are separately placed into two syringes and co-extruded from an extruder to produce a two-layer tube of about 3 mm in diameter and a total wall thickness of about 0.5 mm. The interior layer of the tube consists of Paste II. The exterior layer consists of Paste I. The two-layer tube is extruded directly into a bath including a calcium chloride solution (20% by weight). After about one hour in the bath, the tube was washed with de-ionized water.

EXAMPLE 3

Example 2 is repeated except that three layers are extruded in making the tube: one interior layer using Paste I, one middle alginate layer using Paste II, and one exterior layer using Paste I. The three-layer tube is about 3 mm in diameter with a wall thickness of about 0.5 mm. The tube is then cut to a length to suit the particular application.

EXAMPLE 4

Example 2 is repeated except that a predetermined amount of trimethoprim (a antibacterial agent) is added to Paste I used for extruding the exterior layer to obtain a weight percentage of from about 0.5% to about 30% of the bioactive agent before extrusion of the exterior alginate layer.

Variations, modifications, and other implementations of what is described herein will occur to those of ordinary skill in the art without departing from the spirit and the scope of the invention. Accordingly, the invention is not to be limited only to the preceding illustrative description.

What is claimed is:

1. A bioresorbable medical implant for use in a mammal comprising:
   a. a first layer comprising a first bioresorbable material being substantially free from resorbable particles;
   b. a third layer disposed relative to the first layer, the third layer comprising a third bioresorbable material being substantially free from resorbable particles,
   c. a second layer disposed adjacent the third layer, the second layer comprising a second bioresorbable material and resorbable particles of a first kind are dispersed within the second bioresorbable material, wherein the resorbable particles increase the resorption rate of the second bioresorbable material in the mammal, and the resorbable particles are comprised of the same bioresorbable material of the second bioresorbable material but wherein a molecular weight, crosslinking ratio, or crosslinking ions associated with the resorbable particles is different from that associated with the second bioresorbable material, wherein the medical implant comprises an interior surface and an exterior surface and wherein the first layer forms the interior surface and the second layer forms the exterior surface, and wherein the first bioresorbable material and the third bioresorbable material are different.

2. The medical implant of claim 1, wherein the first bioresorbable material and the second bioresorbable material are identical.

3. The medical implant of claim 1, wherein each of the first, second, and third bioresorbable material comprises an ionically crosslinked polymeric material.

4. The medical implant of claim 1, wherein the at least one of the first, second, or third bioresorbable material is a crosslinked alginate.

5. The medical implant of claim 1, wherein the resorbable particles comprise a radiopacifier.

6. The medical implant of claim 1, further comprising an additional layer disposed between the first and the second layers, the additional layer comprising a bioresorbable material and resorbable particles of a second kind dispersed within the bioresorbable material.

7. The medical implant of claim 6, wherein the bioresorbable material of (a) the additional layer, (b) the first bioresorbable material or the third bioresorbable material, and (c) the second bioresorbable material are identical.

8. The medical implant of claim 3, wherein the ionically crosslinked polymeric material comprises at least one polymer or copolymer made from at least one member of the group consisting of polyacrylic acids, polymethacrylic acid, polyethylene amine, polysaccharides, alginic acid, pectinic acids, carboxy methyl cellulose, hyaluronic acid, heparin, chitosan, carboxymethyl chitosan, carboxymethyl starch, carboxymethyl dextran, heparin sulfate, chondroitin sulfate, cationic starch, and salts thereof.

9. The medical implant of claim 3, wherein the ionically crosslinked polymeric material is an ionically crosslinked polymer hydrogel and has a water content of less than about 90% by weight.

10. The medical implant of claim 1, wherein the first, second, and third layers form one of a stent, a catheter, a cannula, a plug, a constrictor, a sheet, a filler, a bone anchor, a plate, a rod, a seed, a tube, or a portion thereof.

11. The medical implant of claim 1, wherein the medical implant comprises a resorption profile having a plurality of differing resorption rates.

12. The medical implant of claim 11, wherein the resorption rates vary as a function of time.

13. The medical implant of claim 11, wherein the resorption rates vary as a function of a physical dimension of the implant.

14. The medical implant of claim 1, wherein the third layer is disposed adjacent the first layer.

15. The medical implant of claim 11, wherein the resorption profile is non-uniform.

16. The medical implant of claim 1, wherein the first bioresorbable material, the second bioresorbable material, and the third bioresorbable material are different from one another.

17. The medical implant of claim 1, wherein the second bioresorbable material comprises an ionically crosslinked polymeric material.

18. The medical implant of claim 17, wherein the ionically crosslinked polymeric material comprises at least one polymer or copolymer made from at least one member of the group consisting of polyacrylic acids, polymethacrylic acid, polyethylene amine, polysaccharides, alginic acid, pectinic acids, carboxy methyl cellulose, hyaluronic acid, heparin, chitosan, carboxymethyl chitosan, carboxymethyl starch, carboxymethyl dextran, heparin sulfate, chondroitin sulfate, cationic starch, and salts thereof.

* * * * *